(12) United States Patent
De Rezende Neto

(10) Patent No.: US 11,389,609 B2
(45) Date of Patent: Jul. 19, 2022

(54) TRACHEOTOMY DEVICE AND METHOD

(71) Applicant: UNITY HEALTH TORONTO, Toronto (CA)

(72) Inventor: João Baptista De Rezende Neto, Toronto (CA)

(73) Assignee: UNITY HEALTH TORONTO, Toronto (CA)

( * ) Notice: Subject to any disclaimer, the term of this patent is extended or adjusted under 35 U.S.C. 154(b) by 331 days.

(21) Appl. No.: 16/612,494

(22) PCT Filed: May 31, 2018

(86) PCT No.: PCT/CA2018/050641
§ 371 (c)(1),
(2) Date: Nov. 11, 2019

(87) PCT Pub. No.: WO2018/223221
PCT Pub. Date: Dec. 13, 2018

(65) Prior Publication Data
US 2020/0061322 A1 Feb. 27, 2020

Related U.S. Application Data

(60) Provisional application No. 62/582,044, filed on Nov. 6, 2017, provisional application No. 62/514,942, filed on Jun. 4, 2017.

(51) Int. Cl.
*A61M 16/04* (2006.01)

(52) U.S. Cl.
CPC .... *A61M 16/0472* (2013.01); *A61M 16/0488* (2013.01)

(58) Field of Classification Search
CPC .............. A61M 16/04; A61M 16/0465; A61M 16/0468; A61M 16/0472; A61M 16/0429;
(Continued)

(56) References Cited

U.S. PATENT DOCUMENTS 2,840,082 A * 6/1958 Salvatore ......... A61B 17/12009
606/140
3,759,263 A * 9/1973 Taylor .................... A61B 17/32
128/207.29
(Continued)

FOREIGN PATENT DOCUMENTS

BR    PI1001702 A2   12/2013
CA    2071491 A1    6/1991
(Continued)

OTHER PUBLICATIONS

Cook Medical, Products for Bedside Procedures, 2011.
(Continued)

*Primary Examiner* — Colin W Stuart
(74) *Attorney, Agent, or Firm* — ABM Intellectual Property Inc.; Adrienne Bieber McNeil

(57) ABSTRACT

A tracheotomy device includes a head with a head proximal end and a head distal end. The head has a dilating member, and the dilating member has a first dilating member side piece and a second dilating member side piece. The dilating member is moveable between a closed configuration in which the first and second dilating member side pieces are adjacent, and an open configuration in which the first and second dilating member side pieces are spaced apart. The dilating member tapers in cross-sectional area going in a direction from the head proximal end to the head distal end. A sharp tip is at the head distal end. A gripping member is connected to the head proximal end, and is actuatable to move the dilating member between the closed configuration and the open configuration.

12 Claims, 18 Drawing Sheets

(58) Field of Classification Search
CPC ...... A61M 16/0488; A61M 2210/1032; A61M 2205/581; A61M 2205/582; A61M 2205/583; A61M 29/00; A61B 17/3209; A61B 17/32093; A61B 17/3211; A61B 17/3213; A61B 17/34; A61B 17/3417; A61B 17/3494; A61B 17/3496; A61B 17/3474; A61B 17/02; A61B 2017/32113; A61B 2017/32116; A61B 2017/0237; A61B 2017/3454; A61B 2017/3456
USPC .................................................. 128/207.29
See application file for complete search history.

(56) References Cited

U.S. PATENT DOCUMENTS

| | | | |
|---|---|---|---|
| 3,893,454 A * | 7/1975 | Hagelin | A61M 16/0472 600/219 |
| 4,535,773 A | 8/1985 | Yoon | |
| 4,608,982 A * | 9/1986 | Pollard | A61B 17/2812 128/207.29 |
| 4,643,188 A | 2/1987 | Weiss | |
| 4,877,021 A | 10/1989 | Higer et al. | |
| 4,889,112 A * | 12/1989 | Schachner | A61B 17/2812 128/200.26 |
| 4,898,163 A | 2/1990 | George | |
| 5,217,007 A | 6/1993 | Ciaglia | |
| 5,279,285 A * | 1/1994 | Griggs | A61B 17/0206 128/200.26 |
| 5,569,300 A | 10/1996 | Redmon | |
| 5,988,168 A | 11/1999 | Bair | |
| 6,637,435 B2 | 10/2003 | Ciaglia et al. | |
| 8,356,598 B2 * | 1/2013 | Rumsey | A61M 16/0472 128/207.29 |
| 2014/0046303 A1 * | 2/2014 | Donaldson | A61B 17/3415 604/540 |

FOREIGN PATENT DOCUMENTS

| | | |
|---|---|---|
| CN | 2512450 | 9/2002 |
| CN | 105963839 A | 9/2016 |
| WO | 03039641 A1 | 5/2003 |

OTHER PUBLICATIONS

International Search Report & Written Opinion in PCT/CA2018/050641, dated Jul. 17, 2018.

Joao B Rezende-Neto, Argenil J Oliveira, Mario P Neto, Fernando A Botoni and Sandro B Rizoli; A technical modification for percutaneous tracheostomy: prospective case series study on one hundred patients; World Journal of Emergency Surgery; 2011, 6:35.

Extended European Search Report issued in European patent application No. 18814397.8 dated Feb. 9, 2021.

* cited by examiner

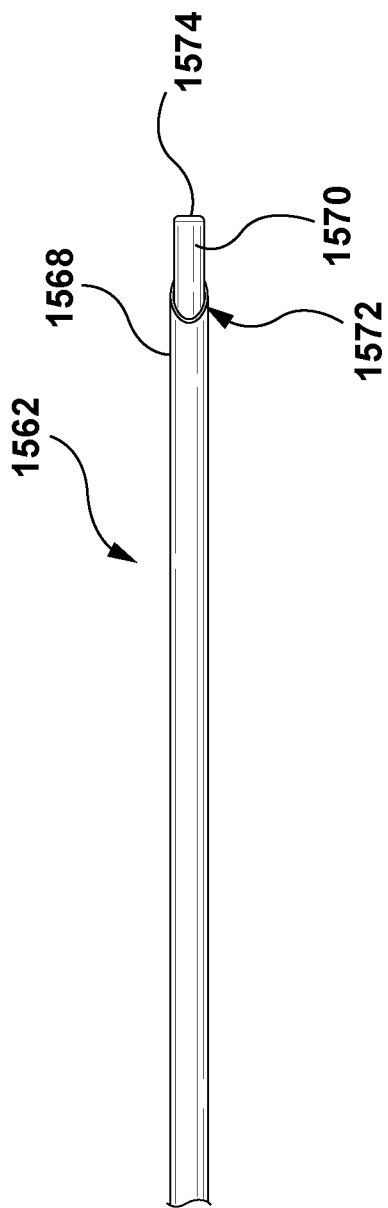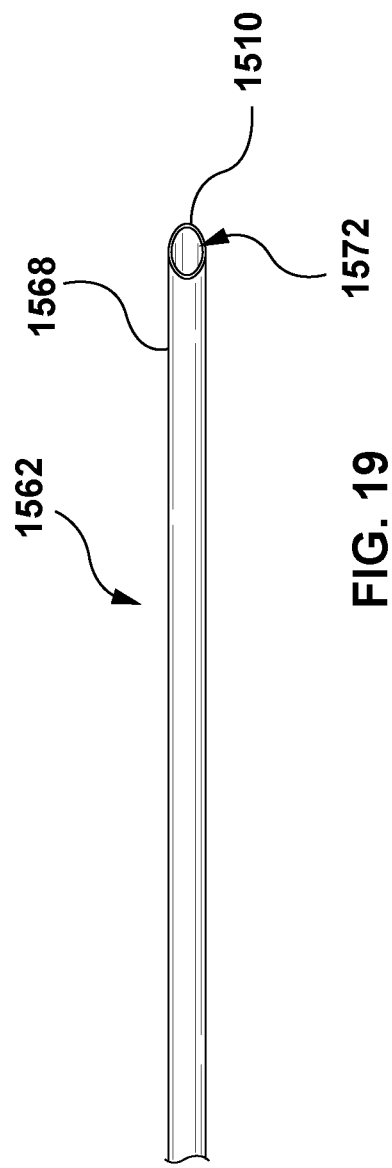

TRACHEOTOMY DEVICE AND METHOD

CROSS-REFERENCES TO RELATED APPLICATIONS

This application is a national stage entry of PCT Patent Application No. PCT/CA2018/050641 filed on May 31, 2018, which claims priority to and the benefit of U.S. Provisional Patent Application No. 62/582,044 filed on Nov. 6, 2017 and U.S. Provisional Patent Application No. 62/514,942 filed on Jun. 4, 2017. Each of the aforementioned applications is hereby incorporated herein by reference in its entirety.

FIELD

This document relates to devices and methods for use in tracheotomy procedures. More specifically, this document relates to a device for preparing the trachea for introduction of a tracheostomy tube, and to a related method.

BACKGROUND

U.S. Pat. No. 6,637,435 (Ciaglia et al.) discloses a dilator for creating tracheostomies in one pass. The dilator includes a generally linear shaft extending from a proximal end and beginning at a distance therefrom, gradually and continuously through a curved distal portion of continuously decreasing diameter (from about 38 french) to a distal tip portion of small diameter of about 12 french at distal end. The outer surface of the insertable portion is treated or hydrophilically coated to minimize friction, and the gradual taper gradually widens the tracheal entrance opening between tracheal rings with minimal trauma. The wall thickness gradually decreases from the linear shaft to the soft distal tip portion. The continuing curve of the distal portion enables the increasingly longer inserted portion of the dilator to remain situated in the trachea during insertion and for the distal tip portion to clear the posterior tracheal wall.

SUMMARY

The following summary is intended to introduce the reader to various aspects of the detailed description, but not to define or delimit any invention.

According to some aspects, a tracheotomy device includes a head with a head proximal end and a head distal end. The head has a dilating member, and the dilating member has a first dilating member side piece and a second dilating member side piece. The dilating member is moveable between a closed configuration in which the first dilating member side piece and the second dilating member side piece are adjacent, and an open configuration in which the first dilating member side piece is spaced from the second dilating member side piece. The dilating member tapers in cross-sectional area going in a direction from the head proximal end towards the head distal end. A sharp tip is at the head distal end, for puncturing tissue. A gripping member is connected to the head proximal end. The gripping member is actuatable to move the dilating member between the closed configuration and the open configuration.

In some examples, the sharp tip is removable from the dilating member. The sharp tip can be retractable from the head distal end towards the head proximal end.

In some examples, the dilating member includes a dilating member passage extending therethrough from a proximal opening in the dilating member to a distal opening in the dilating member. The device can further include an elongate puncturing member removably received in the dilating member passage and having a puncturing member distal end and a puncturing member proximal end. The sharp tip can be provided by the puncturing member distal end.

In some examples, the puncturing member includes an elongate outer cannula having a cannula proximal end and a cannula distal end, and an elongate inner stylet within the cannula. The cannula distal end can provide the sharp tip.

In some examples, the stylet has a blunt stylet distal end and an opposed stylet proximal end. The stylet can be moveable between an extended position wherein the stylet distal end is proud of the sharp tip, and a retracted position wherein the stylet distal end is shy of the sharp tip. The stylet can be biased towards the extended position. The stylet can be moveable from the extended position to the retracted position upon application of force on the stylet distal end in a proximal direction.

In some examples, the stylet has a stylet passage extending longitudinally therethrough and having an opening at the stylet distal end.

In some examples, the sharp tip includes a first tip side piece connected to the first dilating member side piece, and a second tip side piece connected to the second dilating member side piece. When the dilating member is in the closed configuration, the first tip side piece may be adjacent the second tip side piece. When the dilating member is in the open configuration, the first tip side piece may be spaced from the second tip side piece.

In some examples, the head includes a head passage extending therethrough. The head passage may extend from a proximal opening in the dilator to a distal opening at the sharp tip.

In some examples, the dilating member is curved between a dilating member proximal end and a dilating member distal end. The dilating member may be curved so that the sharp tip is spaced from a longitudinal axis of the device.

In some examples, the dilating member is lockable in the closed configuration and/or lockable in the open configuration.

In some examples, the first dilating member side piece and second dilating member side piece each extend from a dilating member proximal end to a dilating member distal end.

In some examples, the first dilating member side piece and second dilating member side piece are mirror images of each other.

In some examples, the dilating member is horn shaped.

In some examples, the gripping member includes a first arm having first arm proximal end portion, a first arm central portion, and a first arm distal end portion. The first arm distal end portion may be connected to the first dilating member side piece. The gripping member may further include a second arm having a second arm proximal end portion, a second arm central portion and a second arm distal end portion. The second arm distal end portion may be connected to the second dilating member side piece. The first arm central portion may be pivotably joined to the second arm central portion.

In some examples, the first arm proximal end includes a first finger loop, and the second arm proximal end includes a second finger loop.

In some examples, the gripping member is removably connected to the head proximal end. The head may be fabricated from plastic. The gripping member may be fabricated from metal.

According to some aspects, a method for creating a tracheostomy includes a) puncturing a trachea with a sharp tip of a tracheotomy device to create a puncture; b) advancing a dilating member of the tracheotomy device into the puncture to dilate the puncture; and c) actuating the dilating member to spread the puncture to an open state.

In some examples, the dilating member has a dilating member distal end, and the method further comprises, prior to step a), positioning the sharp tip at the dilating member distal end.

In some examples, the method further comprises, after step a), detecting passage of the sharp tip through the trachea, and then guarding the sharp tip.

In some examples, the method further comprises, before step c), advancing a guidewire through the tracheotomy device and into the trachea via the puncture.

In some examples, the method further comprises, after step b), retracting the sharp tip from the trachea while maintaining the dilating member in the trachea.

In some examples, after step a), a guidewire is advanced through the tracheotomy device and into the trachea via the puncture.

In some examples, step c) includes spreading apart a first side piece of the dilating member from a second side piece of the dilating member, to force apart tissue around the puncture.

In some examples, step b) includes advancing the dilating member along a curved path.

According to some aspects, a kit of parts for a tracheotomy device includes a head with a head proximal end and a head distal end. The head has a dilating member, and the dilating member has a first dilating member side piece and a second dilating member side piece. The dilating member is moveable between a closed configuration in which the first dilating member side piece and the second dilating member side piece are adjacent, and an open configuration in which the first dilating member side piece is spaced from the second dilating member side piece. The dilating member tapers in cross-sectional area going in a direction from the head proximal end towards the head distal end. The kit further includes an elongate puncturing member having a puncturing member distal end and a puncturing member proximal end. The puncturing member distal end has a sharp tip, and the puncturing member is removably mountable to the head to position the sharp tip at the head distal end. The kit further includes a gripping member actuatable to move the dilating member between the closed configuration and the open configuration.

In some examples, the sharp tip is retractable from the head distal end towards the head proximal end. The dilating member can include a dilating member passage extending therethrough from a proximal opening in the dilating member to a distal opening in the dilating member. The puncturing member can be removably received in the dilating member passage.

In some examples, the puncturing member includes an elongate outer cannula having a cannula proximal end and a cannula distal end, and an elongate inner stylet within the cannula. The cannula distal end can provide the sharp tip.

In some examples, the stylet has a blunt stylet distal end and an opposed stylet proximal end. The stylet can be moveable between an extended position wherein the stylet distal end is proud of the sharp tip, and a retracted position wherein the stylet distal end is shy of the sharp tip. The stylet can be biased towards the extended position. The stylet can be moveable from the extended position to the retracted position upon application of force on the stylet distal end in a proximal direction.

In some examples, the stylet has a stylet passage extending longitudinally therethrough and having an opening at the stylet distal end.

In some examples, the dilating member has a dilating member proximal end and a dilating member distal end, and the dilating member is curved between the dilating member proximal end and the dilating member distal end. The dilating member can be curved so that the sharp tip is spaced from longitudinal axis of the tracheotomy device when assembled.

In some examples, the dilating member is lockable in the closed configuration and/or lockable in the open configuration.

In some examples, the dilating member has a dilating member proximal end and a dilating member distal end, and the first dilating member side piece and second dilating member side piece each extend from the dilating member proximal end to the dilating member distal end. The first dilating member side piece and second dilating member side piece can be mirror images of each other.

In some examples, the dilating member is horn shaped.

In some examples, the gripping member is removably connectable to the head. The gripping member can include a first arm having first arm proximal end portion, a first arm central portion, and a first arm distal end portion. The first arm distal end portion can be connectable to the first dilating member side piece. The gripping member can further include a second arm having a second arm proximal end portion, a second arm central portion and a second arm distal end portion. The second arm distal end portion can be connectable to the second dilating member side piece. The first arm central portion can be pivotably joined to the second arm central portion.

In some examples, the first arm proximal end includes a first finger loop, and the second arm proximal end comprises a second finger loop.

In some examples, the head is fabricated from plastic. In some examples, the gripping member is fabricated from metal.

BRIEF DESCRIPTION OF THE DRAWINGS

The drawings included herewith are for illustrating various examples of articles, methods, and apparatuses of the present specification and are not intended to limit the scope of what is taught in any way. In the drawings:

FIG. 18 is a partial side view of the puncturing member of FIG. 15, with a stylet thereof in an extended position;

FIG. 19 is a partial side view of the puncturing member of FIG. 15, with a stylet thereof in a retracted position;

DETAILED DESCRIPTION

Various apparatuses or processes will be described below to provide an example of an embodiment of the claimed subject matter. No embodiment described below limits any claim and any claim may cover processes or apparatuses that differ from those described below. The claims are not limited to apparatuses or processes having all of the features of any one apparatus or process described below or to features common to multiple or all of the apparatuses described below. It is possible that an apparatus or process described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Described herein are tracheotomy devices and related methods. The tracheotomy devices may in some examples allow for relatively simple and safe creation of a tracheostomy in a patient. For example, as will be described hereinbelow, a tracheotomy device as described herein may in some examples be used as an all-in-one tool that can puncture a trachea, dilate the puncture, and open the puncture.

As used herein, the term "tracheostomy" refers to a surgically created hole through the trachea. The term "tracheotomy" refers to a surgical procedure that creates a tracheostomy.

Figure 1:
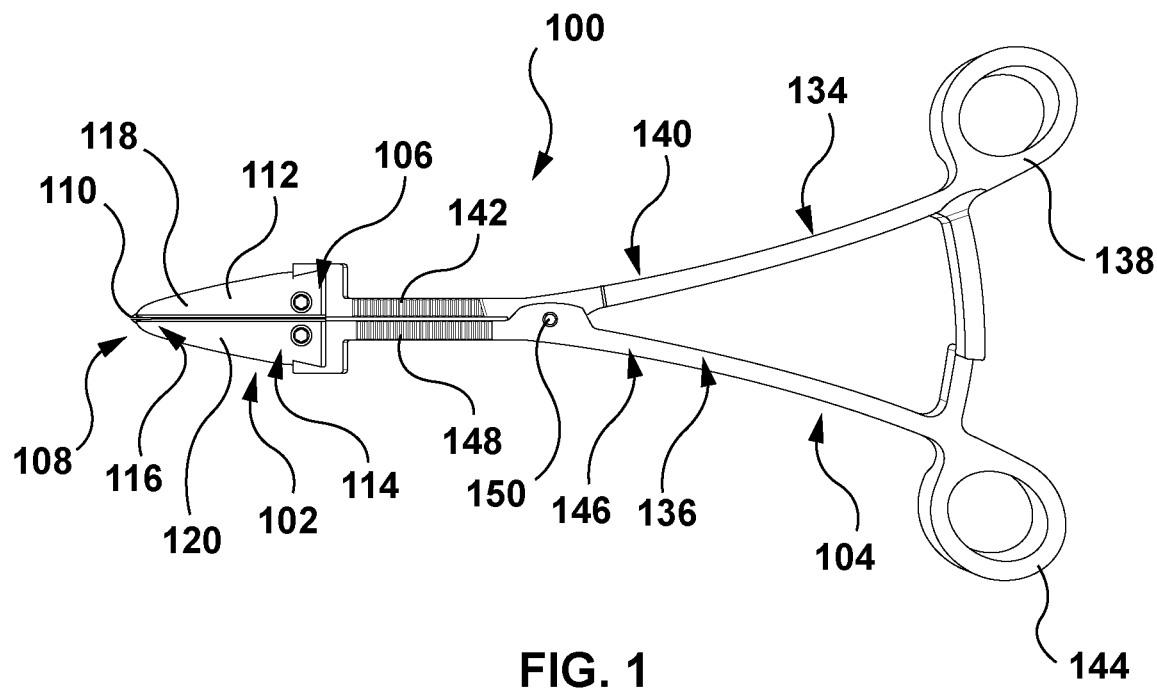
FIG. 1 is a top view of an example tracheotomy device, with a dilator thereof in a closed configuration.
Figure 2:
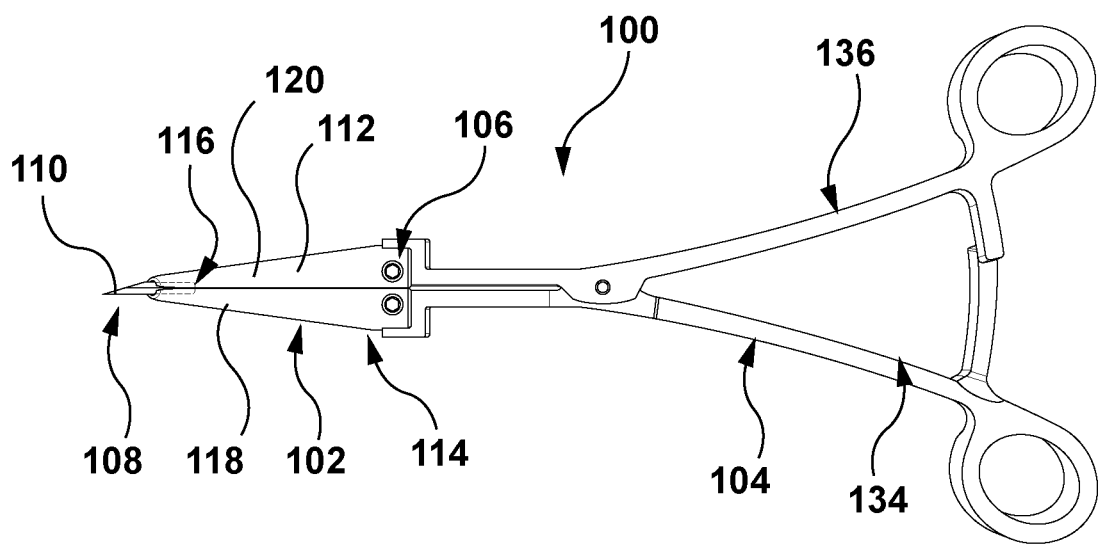
FIG. 2 is a bottom view of the tracheotomy device of FIG. 1, with the dilator thereof in a closed configuration.

Referring now to FIGS. 1 and 2, a first example tracheotomy device 100 is shown. The device 100 may in some examples be used to create a tracheostomy, and to facilitate insertion of a tracheostomy tube through the tracheostomy. When used to create a tracheostomy, the device 100 may puncture the trachea, dilate the puncture, and open the puncture. This may obviate or reduce the need for several separate devices that each perform a single one of these functions.

Referring still to FIGS. 1 and 2, in the example shown, the tracheotomy device 100 includes a head 102, and a gripping member 104 connected to the head 102. The head 102 may be used to puncture, dilate, and open the trachea, and the gripping member 104 may be gripped by the surgeon or another user and may used to manipulate the head 102.

Figure 3:
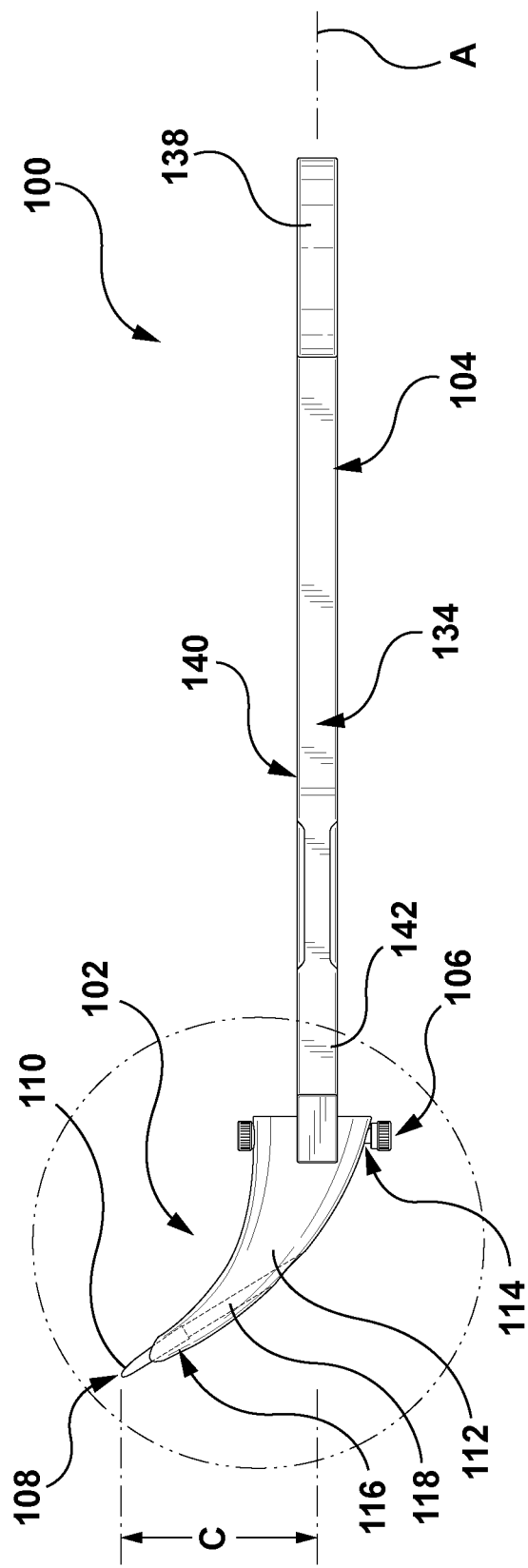
FIG. 3 is a side view of the tracheotomy device of FIG. 1, with the dilator thereof in a closed configuration.
Figure 4:
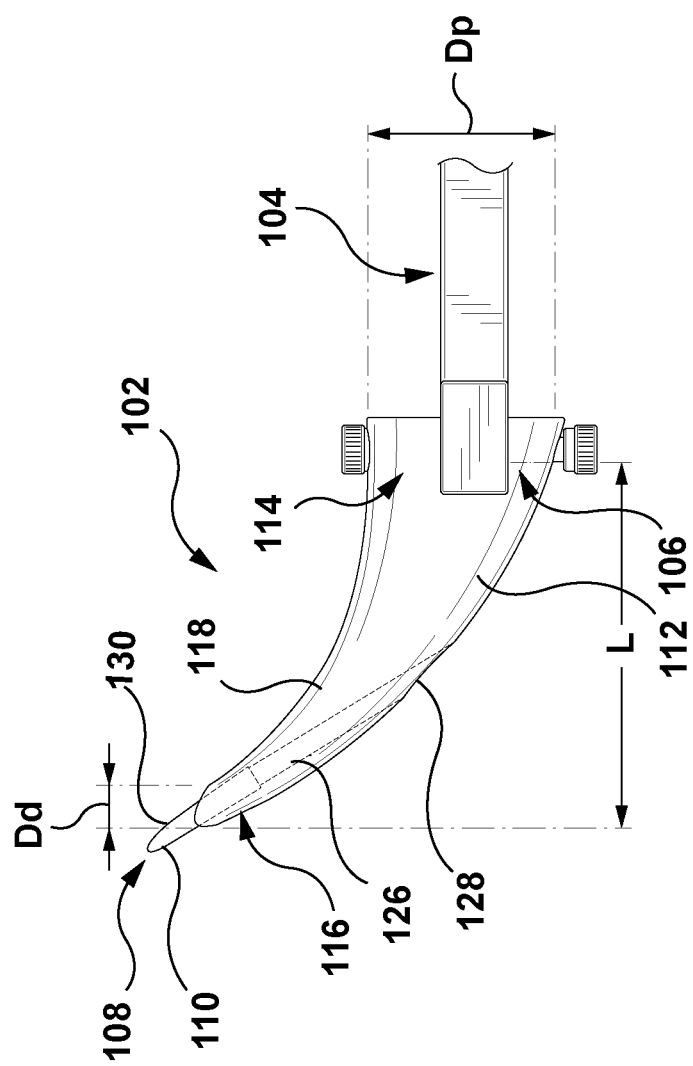
FIG. 4 is an enlarged side view of the head of the tracheotomy device of FIG. 1, with the dilator thereof in a closed configuration.

Referring also to FIGS. 3 and 4, in the example shown, the head 102 has a head proximal end 106, and a head distal end 108. As used herein, the direction going toward the proximal end 106 from the distal end 108 will be referred to as the 'proximal direction', and the direction going toward the distal end 108 from the proximal end 106 may be referred to as the 'distal direction'.

A sharp tip 110 is at the head distal end 108. The sharp tip 110 may be used to puncture tissue. In the example shown, the head 102 includes a short hypodermic needle with a beveled end, which forms the sharp tip 110.

Referring still to FIGS. 1 to 4, in the example shown, the head 102 further includes a dilating member 112. In the example shown, the dilating member 112 is separately formed from the sharp tip 110, and the sharp tip 110 is secured to the dilating member 112 with an adhesive. In alternative examples (not shown), the dilating member 112 and sharp tip 110 can be secured together in another manner (e.g. with a mechanical fastener). In further alternative examples (not shown), the sharp tip and the dilating member may be integral, and the sharp tip may effectively form an end of the dilating member.

The dilating member 112 has a dilating member proximal end 114, and a dilating member distal end 116. In the example shown, the dilating member proximal end 114 is coincident with the head proximal end 106, and the dilating member distal end 116 is positioned proximal of the head distal end 108, and is joined to the hypodermic needle (which forms the sharp tip 110). In alternative examples, the sharp tip 110 may be further spaced from the dilating member distal end 116, optionally with another structure between the sharp tip 110 and the dilating member distal end 116. In further alternative examples, the sharp tip 110 may be right at the dilating member distal end 116 (i.e. the dilating member distal end 116 may be coincident with the head distal end 106).

In some examples (not shown), the sharp tip may be retractable towards the dilator, for example into the dilator. Retraction of the tip may be automatic, after the tip has pierced the trachea. This may aid in preventing damage to the posterior wall of the trachea. In other examples, as will be described below, the sharp tip may be removable from the dilator.

Figure 6:
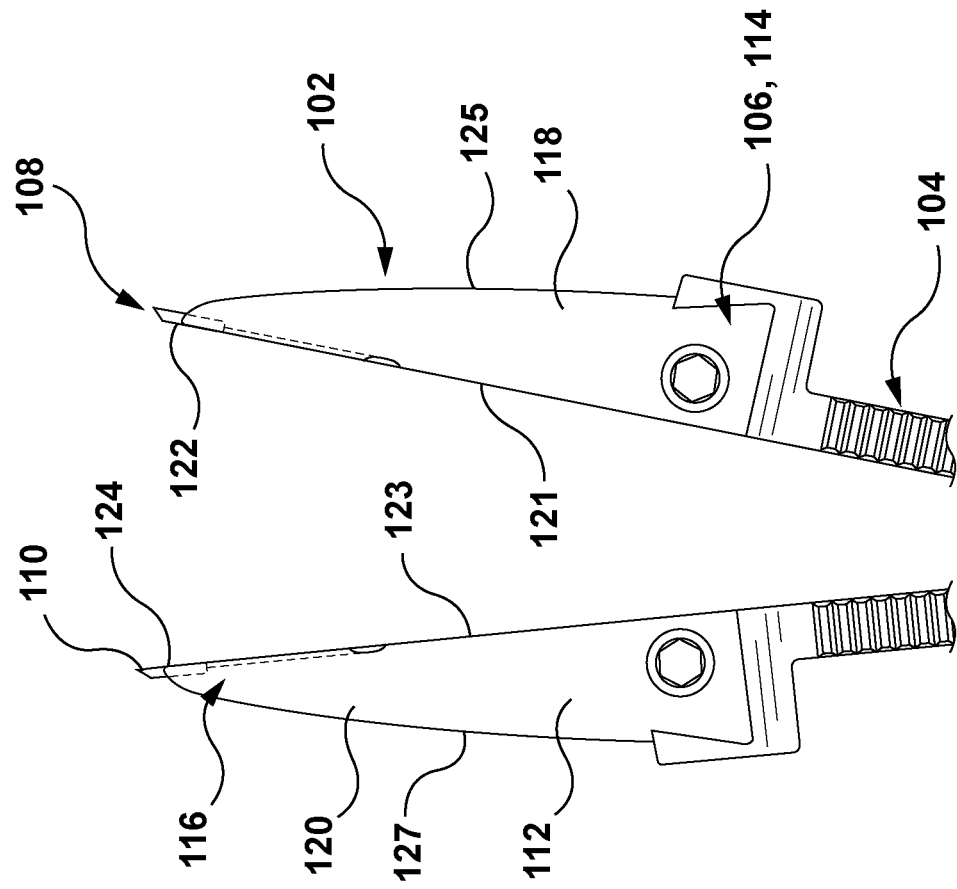
FIG. 6 is an enlarged top view of the head of the tracheotomy device of FIG. 1, with the dilator thereof in an open configuration.
Figure 5:
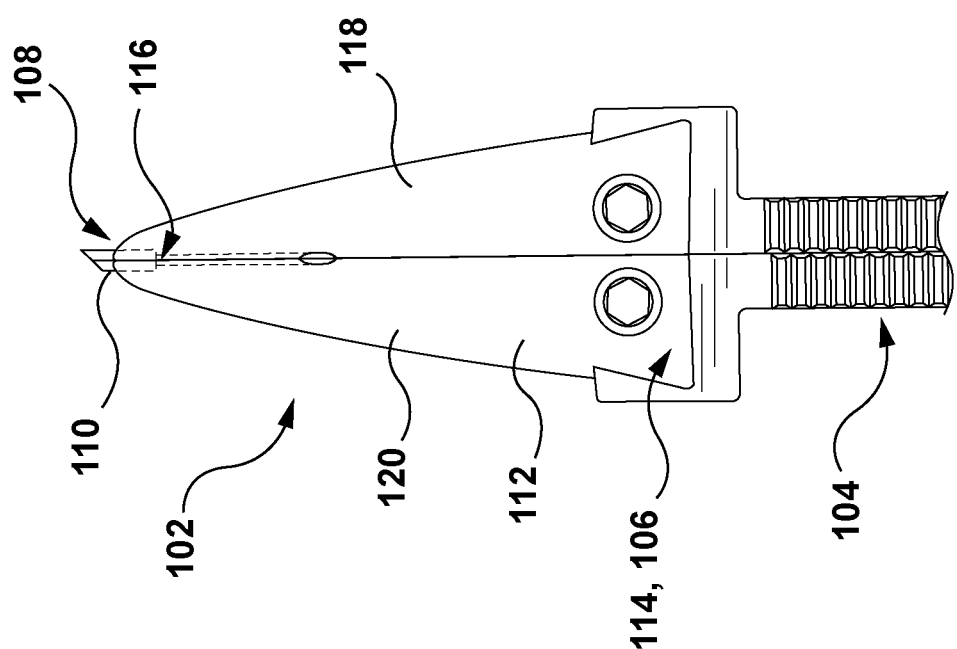
FIG. 5 is an enlarged top view of the head of the tracheotomy device of FIG. 1, with the dilator thereof in a closed configuration.
Figure 7:
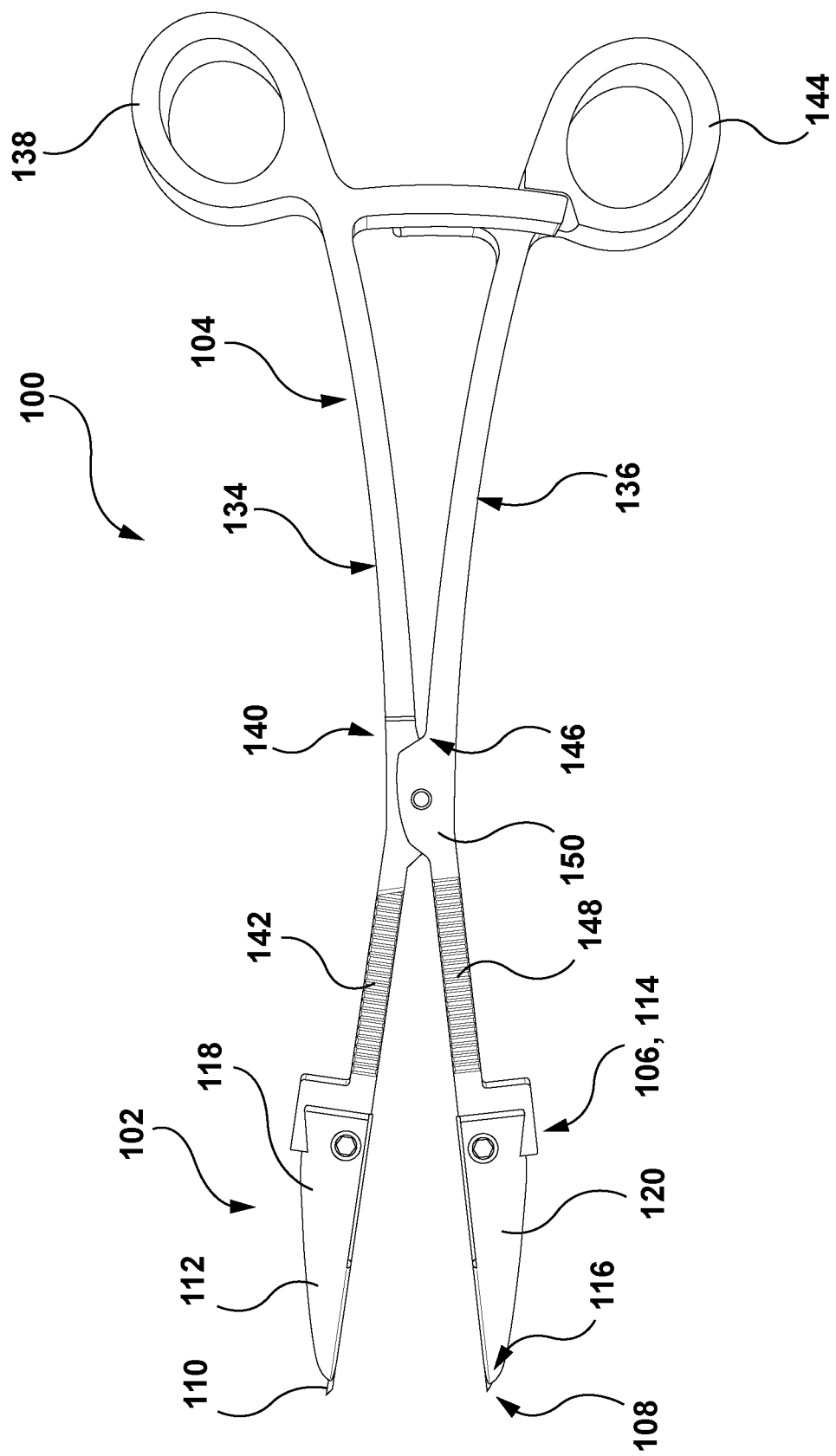
FIG. 7 is a top view similar to that of FIG. 1, but with the dilator of the tracheotomy device in an open configuration.

Referring to FIGS. 5 to 7, in the example shown, the dilating member 112 includes a first dilating member side piece 118, and a second dilating member side piece 120. The first dilating member side piece 118 and second dilating member side piece 120 are separable from each other, and the dilating member 112 is moveable between a closed configuration, shown in FIG. 5 (and also in FIGS. 1 to 4), in which the first dilating member side piece 118 and the second dilating member side piece 120 are adjacent each other (optionally in abutment), and an open configuration, shown in FIGS. 6 and 7, in which the first dilating member side piece 118 is spaced from the second dilating member side piece 120. As will be described in further detail below, movement of the dilating member 112 from the closed configuration to the open configuration can be effected by manipulating the gripping member 104, and can be carried out in order to dilate a puncture in a trachea.

In the example shown, the first dilating member side piece 118 and the second dilating member side piece 120 are each approximately semi-circular in transverse section, and each includes an inner planar surface 121, 123, respectively, and an outer rounded surface 125, 127, respectively (shown in FIG. 6). The planar surfaces 121, 123 face each other, and are in abutment or close proximity when the dilating member 112 is in the closed configuration. When the dilating member 112 is moved to the open position, the planar surfaces 121, 123 move apart from each other in a direction generally transverse to the planar surfaces 121, 123.

In the example shown, the first dilating member side piece 118 and second dilating member side piece 120 are similar in shape and size, and are mirror images of each other. The first dilating member side piece 118 and second dilating member side piece 120 each extend from the dilating member proximal end 114 to the dilating member distal end 116.

In alternative examples, the first dilating member side piece 118 may be of a different size and shape from the second dilating member side piece 120, and the first dilating member side piece 118 and second dilating member side piece 120 may not be mirror images of each other. Furthermore, the first dilating member side piece 118 and second dilating member side piece 120 may be of a cross-sectional shape other than semi-circular. For example, the first dilating member side piece 118 and/or second dilating member side piece 120 may be semi-oval. For further example, the first dilating member side piece 118 and/or second dilating member side piece 120 may be another shape that forms a generally rounded outer surface and optionally a planar inner surface.

Furthermore, in alternative examples, one or both of the first dilating member side piece 118 and second dilating member side piece 120 may extend from a position distal to the dilating member proximal end 114, and/or to a position proximal of the dilating member distal end 116.

Referring to FIGS. 4 and 5, in the example shown, when in the closed configuration, the dilating member 112 is generally horn-shaped. That is, the dilating member 112 gradually tapers in cross-sectional area going from the dilating member proximal end 114 to the dilating member distal end 116, and also is curved between the dilating member proximal end 114 and the dilating member distal end 116. The taper in the dilating member 112 can allow for a puncture in the trachea to be dilated as the dilating member 112 is advanced through the puncture, and the curve can aid in directing the sharp tip 110 away from the posterior wall of the trachea as the dilating member 112 is advanced, and can aid in directing a guidewire downwardly towards the lungs from the tracheostomy.

In some examples, the dilating member 112 may have a length L (shown in FIG. 4) of between about 20 mm and about 70 mm, or of between about 35 mm and about 55 mm, or of about 45 mm. In some examples, the dilating member 112 may have a distal diameter $D_d$ (shown in FIG. 4) of between about 0.5 mm and about 3.5 mm, or of between about 1 mm and about 3 mm, or of about 2 mm. In some examples, the dilating member 112 may have a proximal diameter $D_p$ (shown in FIG. 4) of between about 5 mm and about 35 mm, or of between about 15 mm and about 25 mm, or of about 20 mm. In some examples, the dilating member 112 may be curved such that the dilating member distal end 116 is displaced from the longitudinal axis A of the device by a distance C (shown in FIG. 3) of between about 10 mm and about 50 mm, or of between about 20 mm and about 40 mm, or of about 30 mm.

Referring to FIG. 6, in the example shown, similarly to the dilating member 112, the sharp tip 110 includes a first tip side piece 122 and a second tip side piece 124. The first tip side piece 122 is connected to the first dilating member side piece 118, and the second tip side piece 124 is connected to the second dilating member side piece 120. When the dilating member 112 is in the closed configuration, the first tip side piece 122 is in abutment with the second tip side piece 124. When the dilating member 112 is in the open configuration, the first tip side piece 122 is spaced from the second tip side piece 124.

Figure 8:
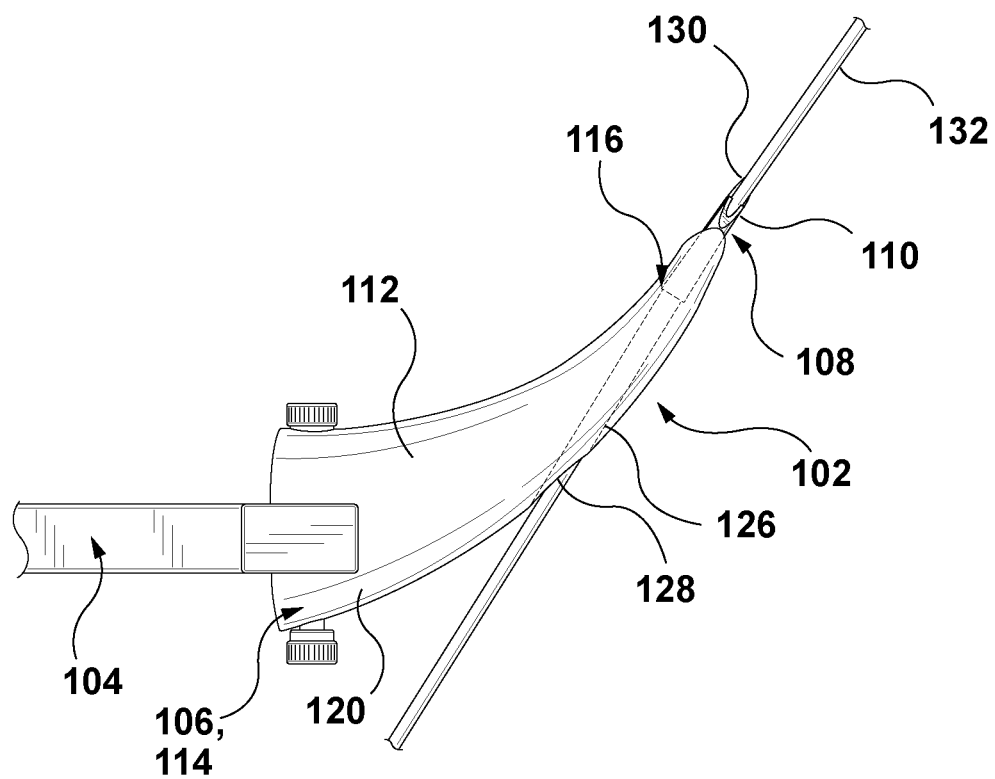
FIG. 8 is an enlarged side view of the head of the tracheotomy device of FIG. 1, with the dilator thereof in a closed configuration, and with a guidewire extending through a passage of the head.
Figure 9:
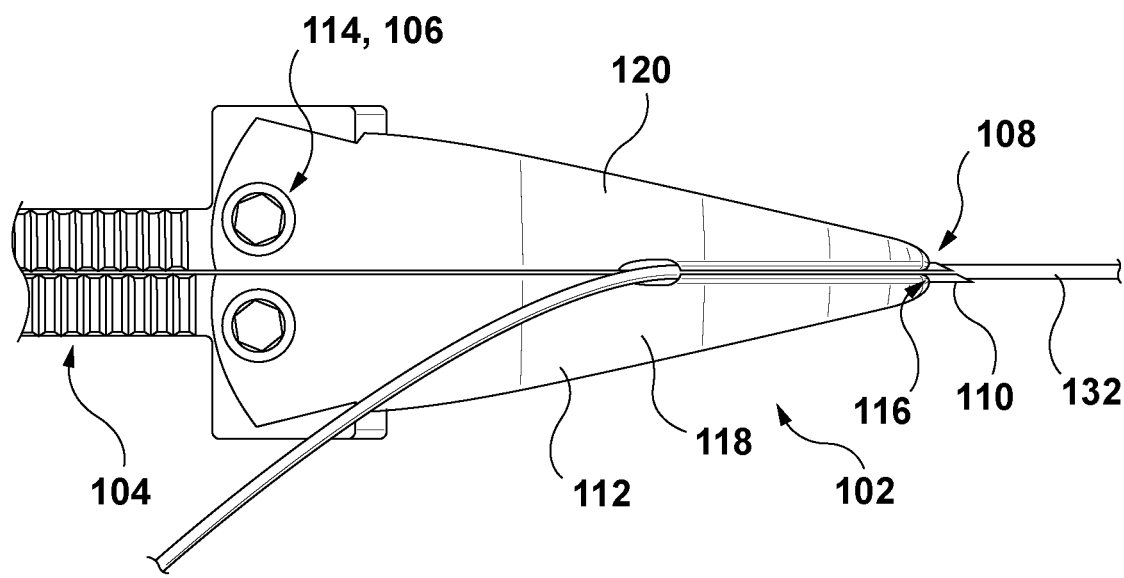
FIG. 9 is an enlarged top view of the head of the tracheotomy device of FIG. 1, with the dilator thereof in a closed configuration, and with a guidewire extending through a passage of the head.

Referring to FIG. 4, in the example shown, the head 102 includes a passage 126 (also referred to herein as a 'head passage') extending therethrough. In the example shown, the passage 126 is formed by the first dilating member side piece 118 and the second dilating member side piece 120 when the dilator is in the closed configuration. The passage 126 is generally linear, and extends from a proximal opening 128 in the dilating member 112 to a distal opening 130 at the tip 110. The passage can be used to pass a guidewire 132 through the head 102, as shown in FIGS. 8 and 9.

Referring now to FIGS. 1 and 7, in the example shown, the gripping member 104 includes a first arm 134 and a second arm 136. The first arm 134 has a first arm proximal end 138, a first arm central portion 140, and a first arm distal end 142. The second arm 136 has a second arm proximal end 144, a second arm central portion 146, and a second arm distal end 148. The first arm distal end 142 is connected to the first dilating member side piece 118, and the second arm distal end 148 is connected to the second dilating member side piece 120. Furthermore, the first arm central portion 140 is pivotably joined to the second arm central portion 146, at a pivot joint 150. The first arm proximal end 138 includes a first finger loop, and the second arm proximal end 144 includes a second finger loop.

Referring still to FIGS. 1 and 7, in the example shown, movement of the first arm proximal end 138 and the second arm proximal end 144 towards and away from each other (e.g. by a user grasping the first and second finger loops and moving them towards and away from each other) causes movement of the dilating member 112 between the closed configuration (as shown in FIG. 1) and the open configuration (as shown in FIG. 7).

In some examples (not shown), the dilating member 112 may be lockable in the closed configuration and/or in the open configuration. For example, the head 102 and/or the gripping member 104 may include one or more locking members.

As mentioned above, the first arm distal end 142 is connected to the first dilating member side piece 118, and the second arm distal end 148 is connected to the second dilating member side piece 120. For example, as shown, the first arm 134 and second arm 136 may be separately formed from the first 118 and second 120 dilating member side pieces, and secured thereto by mechanical fasteners. In other examples, the first 134 and second 136 arms may be integral with the first 118 and second 120 dilating member side pieces, respectively.

In some examples, the gripping member 104 may be removably connected to the head 102. This may, for example, allow for the head 102 to be disposed of after each use, and for the gripping member 104 to be sterilized and reused. In such examples, the head 102 may be fabricated from a disposable material such as plastic, and the gripping member 104 may be fabricated from a sterilisable material such as metal.

A method for creating a tracheostomy will now be described with reference to FIGS. 10 to 14. The method will be described with reference to device 100; however, the device 100 may be used according to other methods, and the method may be carried out with other devices.

The method may be carried out at the bedside, in the operating room, or in an emergency department. The method may begin after prepping of the patient, including sedation, preparation of the operative site, ultrasound, etc.

Figure 10:
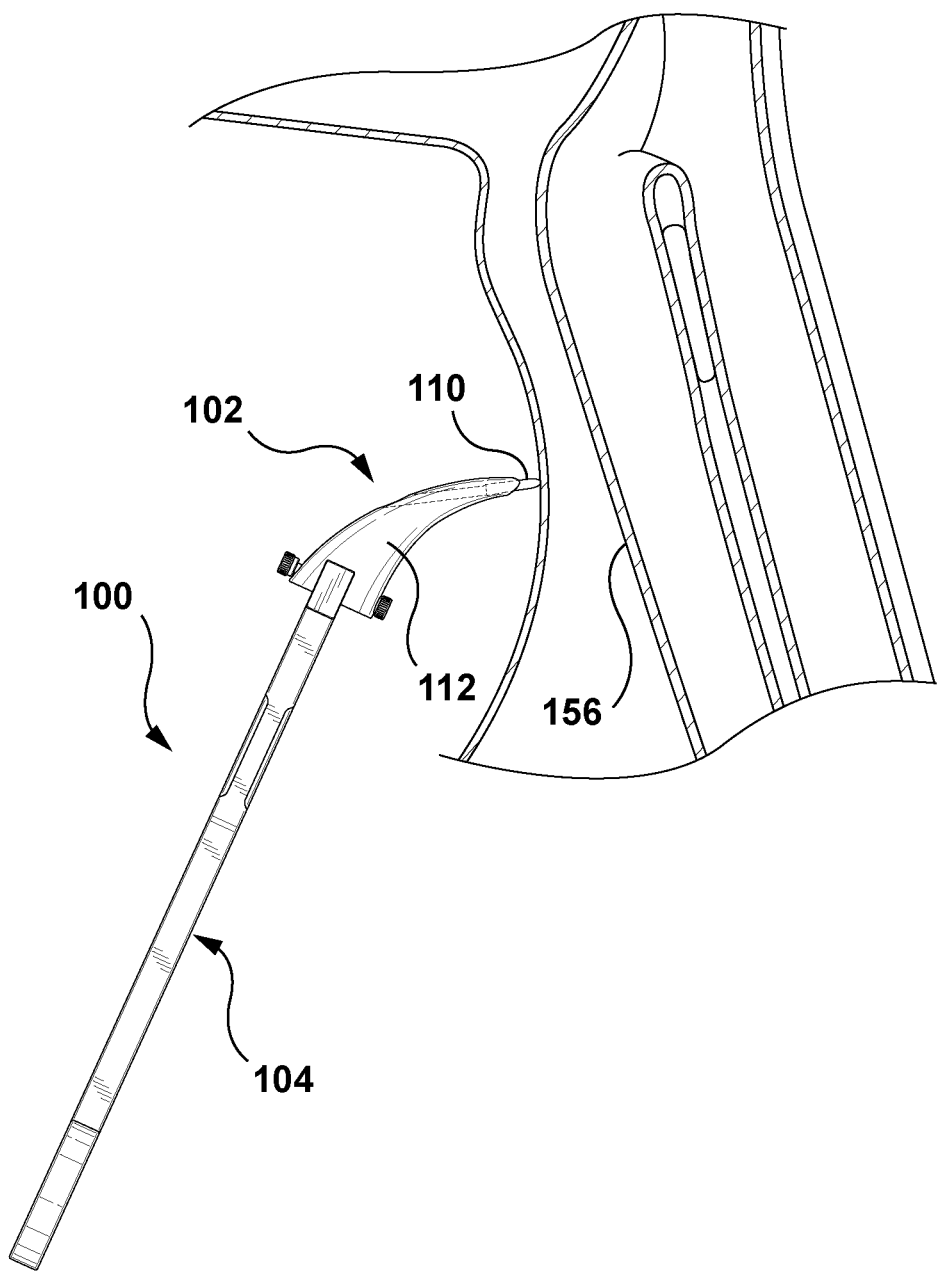
FIG. 10 is a schematic side view of the device of FIG. 1 in use, with a sharp tip of the device puncturing the skin adjacent the trachea.
Figure 11:
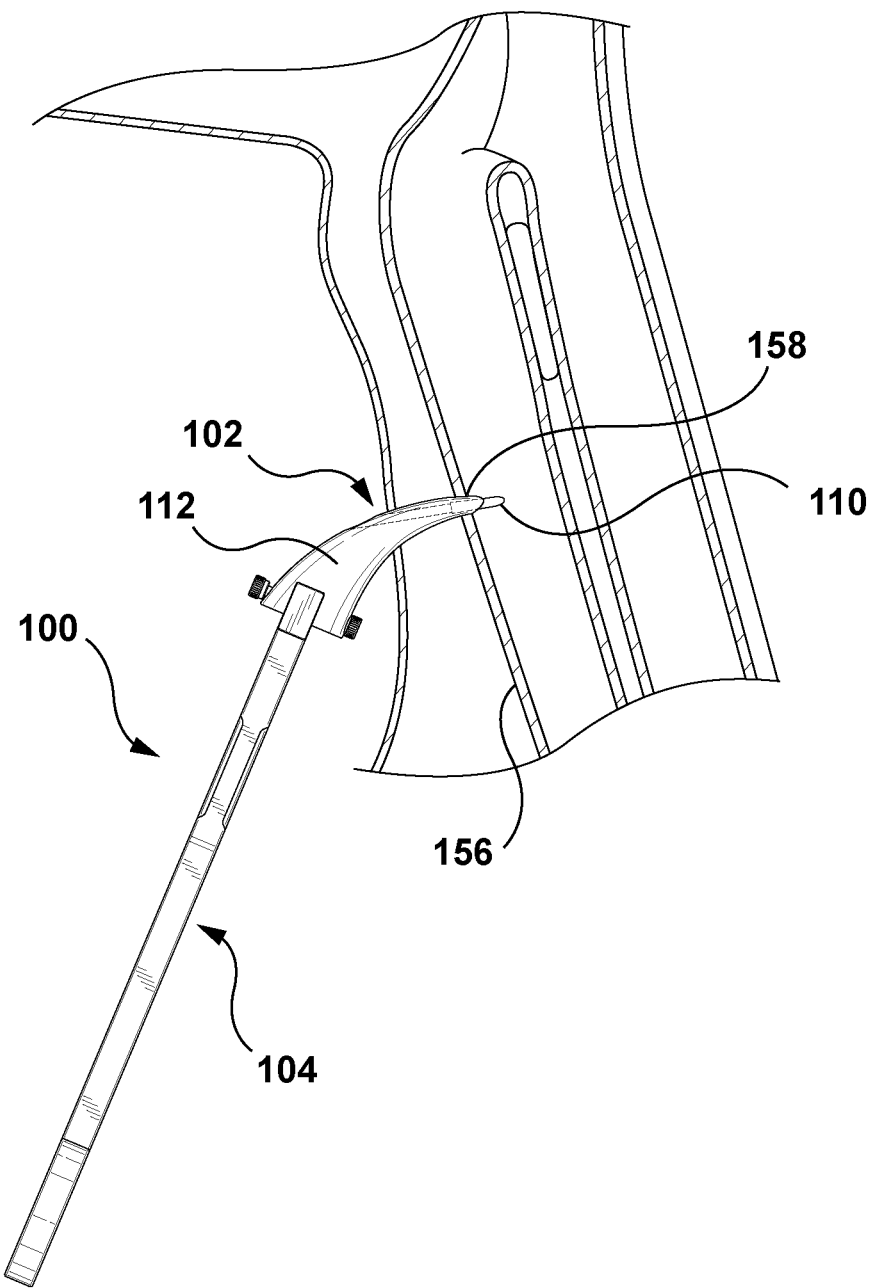
FIG. 11 is a schematic side view of the device of FIG. 1 in use, with the sharp tip of the device puncturing the trachea.

Referring to FIGS. 10 and 11, as a first step, with the dilating member 112 in the closed configuration, the sharp tip 110 of device 100 may be used to puncture the skin, subcutaneous tissue, and anterior wall 156 of the trachea, to create a puncture 158 in the trachea. A guidewire 132 (not shown in FIGS. 10 and 11) may be advanced through the passage 126 of the head 102 and into the trachea, towards the patients lungs.

Figure 12:
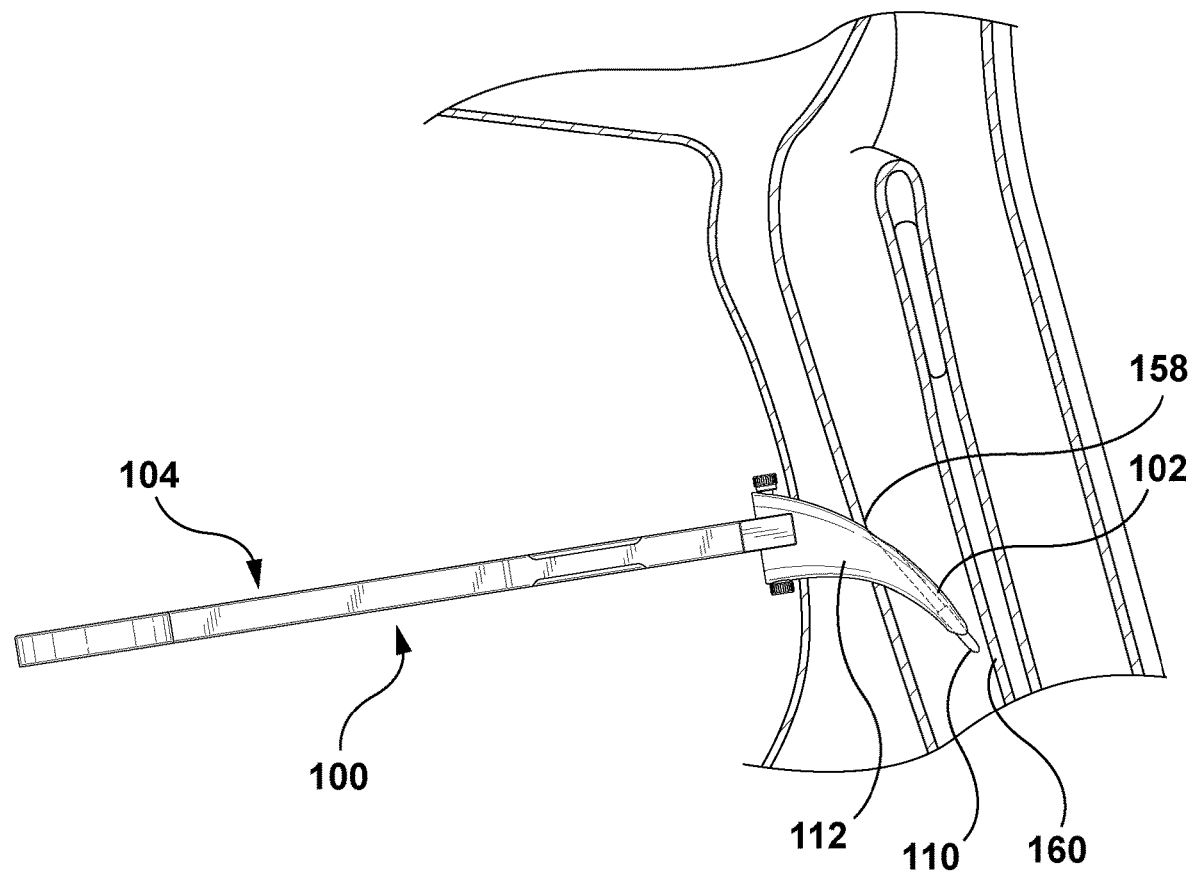
FIG. 12 is a schematic side view of the device of FIG. 1 in use, with the dilator of the device being advanced into the trachea along a curved path.

Referring to FIG. 12, the dilating member 112 may then be advanced into the puncture 158, to dilate the puncture 158. The dilating member 112 may be advanced along a curved path, so that the sharp tip 110 is steered generally downwardly away from the posterior wall 160 of the trachea.

Figure 13:
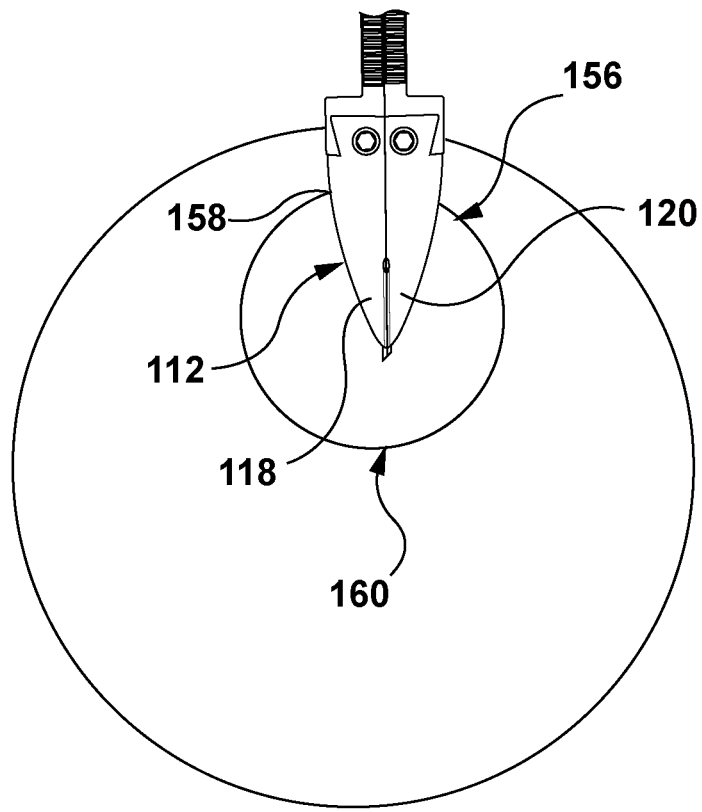
FIG. 13 is a schematic sectional view, looking downwardly in the throat, of the device of FIG. 1 in use, with the dilator of the device in position in the trachea and in a closed configuration.
Figure 14:
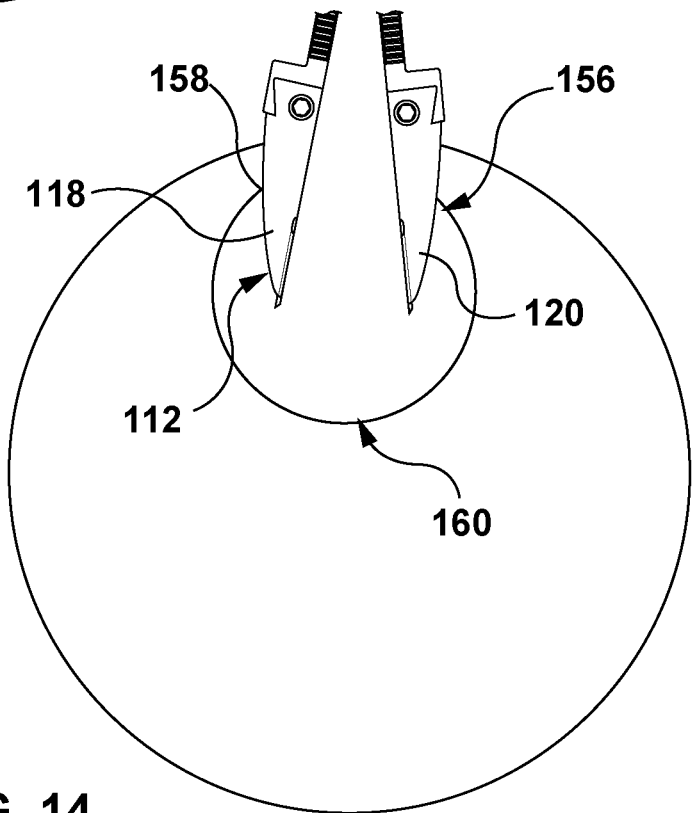
FIG. 14 is a schematic sectional view, looking downwardly in the throat, of the device of FIG. 1 in use, with the dilator of the device in position in the trachea and in an open configuration.

Referring to FIGS. 13 and 14, the dilating member 112 may then be actuated to spread the puncture 158 to an open state. Particularly, the gripping member 104 (not shown in FIGS. 13 and 14) may be manipulated to move the dilating member 112 from the closed configuration, shown in FIG. 13, to the open configuration, shown in FIG. 14, where the first dilating member side piece 118 is spaced apart from the second dilating member side piece 120. This forces apart the tissue around the puncture 158, so that the interior of the trachea can be visualized. The dilating member 112 may then optionally be locked in the open configuration.

With the dilating member 112 in the open configuration, and the puncture 158 in the trachea in an open state, an introducer (not shown) may be advanced into the trachea, between the first dilating member side piece 118 and second dilating member side piece 120. Due to the open state of the trachea, advancement of the introducer may be relatively safe and simple, because the surgeon can visualize the path of the introducer and ensure that the introducer is in the trachea and directed towards the lungs.

The device 100 may then be removed from the patient, and a tracheotomy tube (not shown) may be advanced over the introducer.

Referring now to FIGS. 15 to 19, another example tracheotomy device 1500 is shown. In FIGS. 15 to 19, like features to the example of FIGS. 1 to 9 will be referred to with like reference numerals, incremented by 1400.

Figure 15:
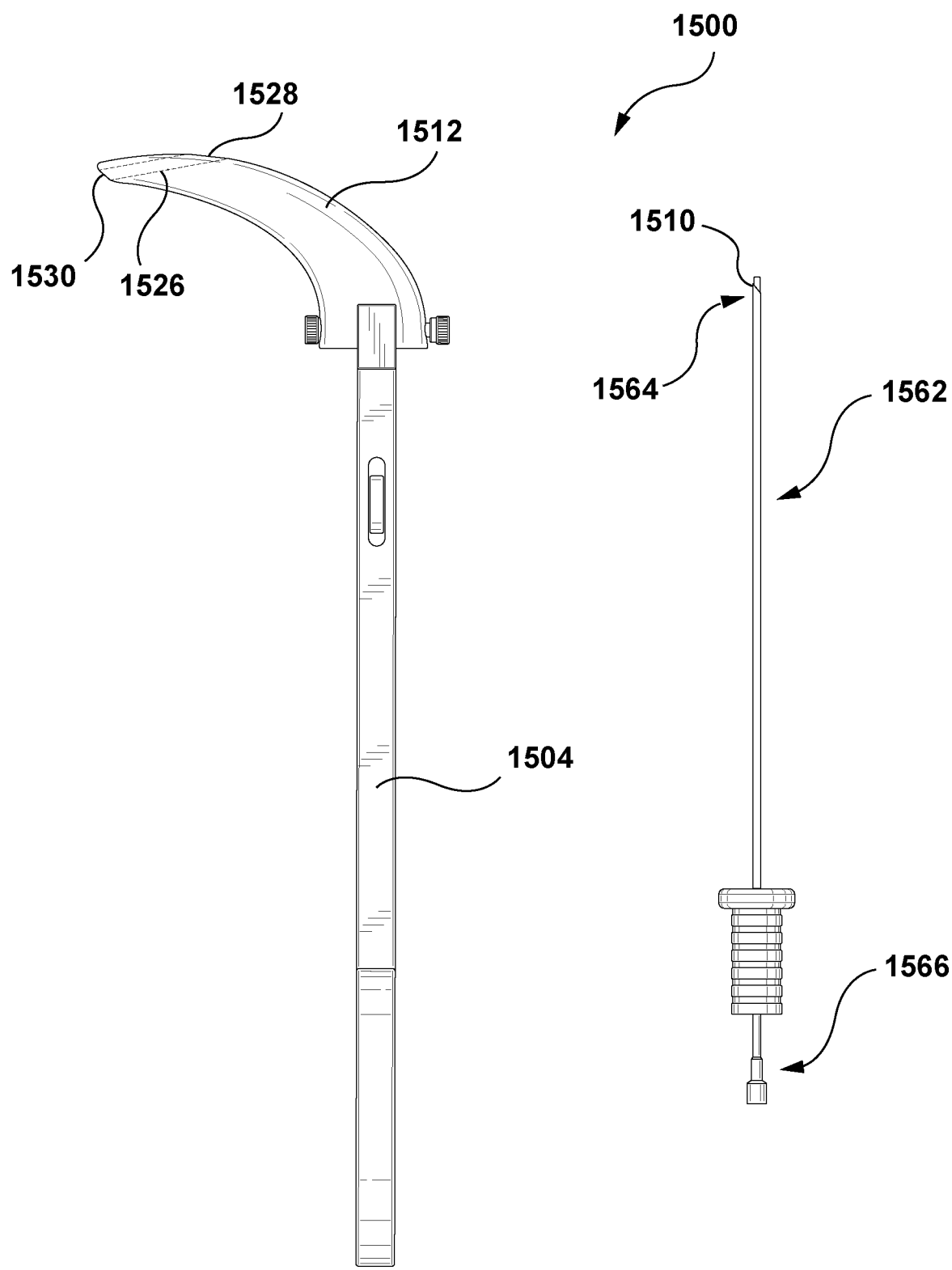
FIG. 15 is a side view of a kit of parts for another example tracheotomy device, with a puncturing member provided separately from the dilating member and gripping member.

Referring to FIG. 15, in the tracheotomy device 1500, the dilating member 1512 and gripping member 1504 are similar to the dilating member 112 and gripping member 104 of FIGS. 1 to 14, and will not be described in detail. However, in the tracheotomy device 1500, the sharp tip 1510 is removable from the dilating member 1512. Particularly, the sharp tip 1510 is provided by a puncturing member 1562. The puncturing member 1562 is generally elongate, and has a puncturing member distal end 1564 and a puncturing member proximal end 1566. The puncturing member distal end 1564 provides the sharp tip 1510.

Figure 16:
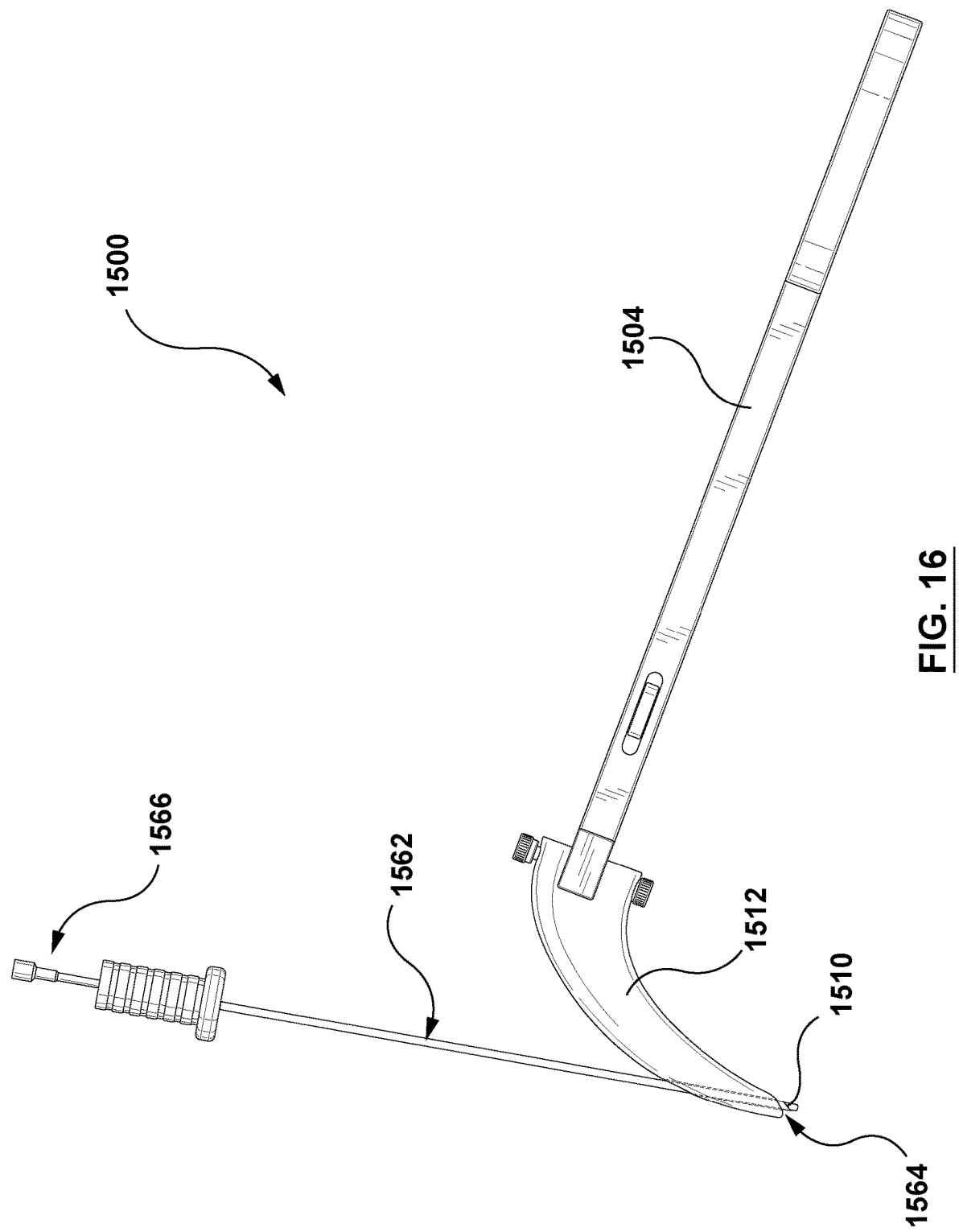
FIG. 16 is a side view of the parts of FIG. 15, with the puncturing member received in a passage of the dilating member.
Figure 17:
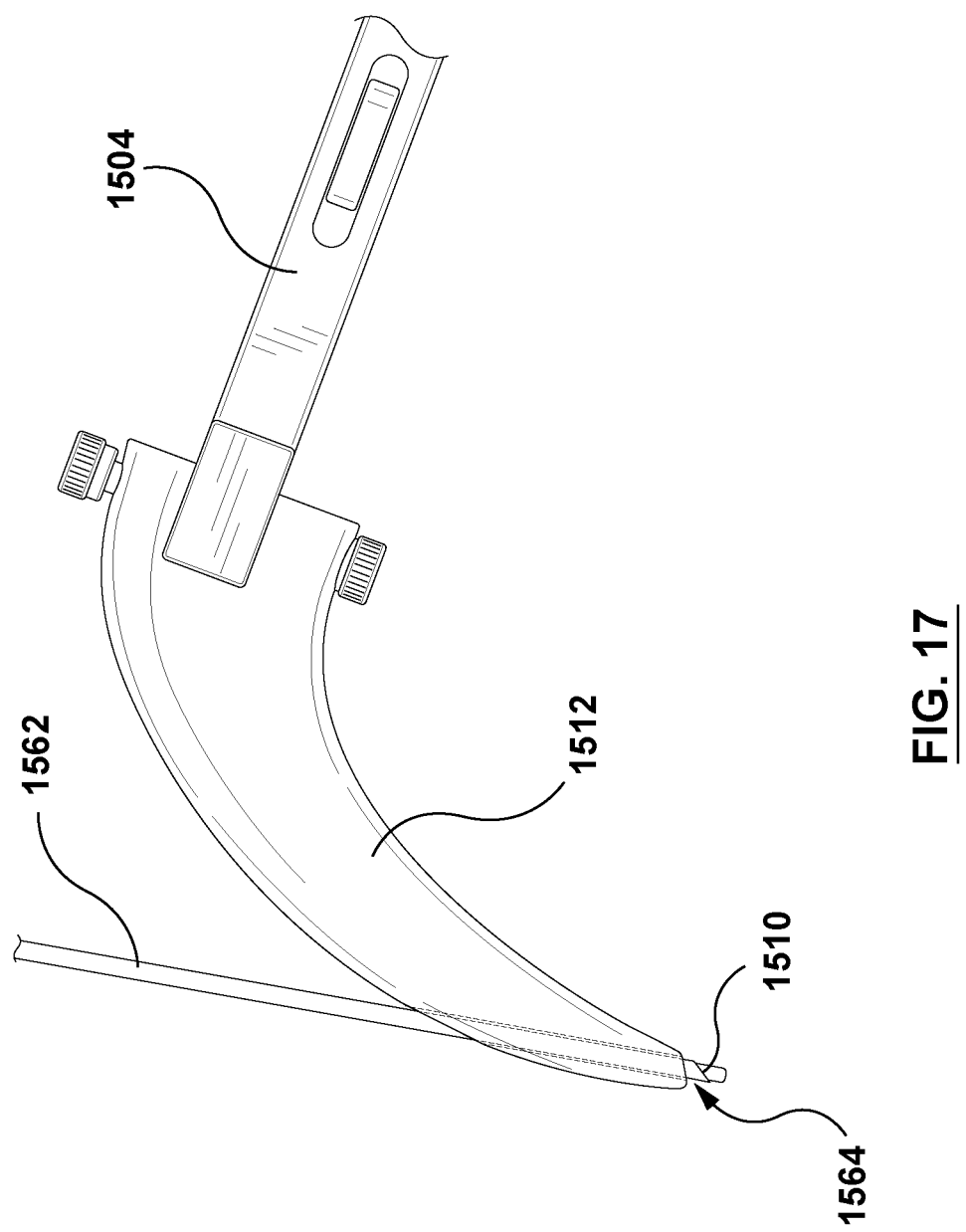
FIG. 17 is an enlarged view of the dilating member and a portion of the puncturing member of FIG. 16.

The dilating member 1512 has a dilating member passage 1526 extending therethrough, from a proximal opening 1528 in the dilating member 1512 to a distal opening 1530 in the dilating member 1512. The dilating member passage 1526 is similar to the passage 126 of the head 102, described above. Referring to FIGS. 16 and 17, the puncturing member 1562 is removably receivable in the dilating member passage 1526. For example, the puncturing member distal end 1564 can be inserted into the proximal opening 1528, and through the dilating member passage 1526, so that it projects from the distal opening 1530 (the proximal opening 1528, passage 1526, and distal opening 1530 are not labelled in FIGS. 16 and 17).

Referring to FIGS. 18 and 19, in the example shown, the puncturing member 1562 is similar to a Veress needle known in the art. That is, the puncturing member 1562 includes an outer cannula 1568 and an inner stylet 1570 (the inner stylet 1570 is not visible in FIG. 19). The outer cannula 1568 is elongate, and has a cannula proximal end (not shown) and a cannula distal end 1572. The cannula distal end 1572 provides the sharp tip 1510. The stylet 1570 is elongate, and has a blunt stylet distal end 1574 and an opposed stylet proximal end (not shown). The stylet 1570 is moveable between an extended position (shown in FIG. 18), in which the stylet distal end 1574 is proud of the sharp tip 1510, and a retracted position (shown in FIG. 19), in which the stylet distal end 1574 is shy of the sharp tip 1510. When the stylet 1570 is in the extended position, the stylet distal end 1574 can guard tissue from being inadvertently damaged by the sharp tip 1510.

Similarly to a Veress needle, the stylet 1570 is biased towards the extended position (e.g. by a spring, not shown), and is moveable to the retracted position upon the application of force applied to the stylet distal end 1574 in the proximal direction. When the force is removed, the stylet 1570 snaps or pops springs back to the extended position.

In the example shown, the stylet 1570 further includes a stylet passage (not shown) extending longitudinally therethrough. The passage has an opening at the stylet distal end 1574. A guidewire may be inserted through the passage and out of the opening.

The puncturing member 1564, dilating member 1512, and gripping member 1504 may optionally be provided as a kit. The dilating member 1512 and gripping member 1504, and any parts thereof, may be provided as separate pieces.

Figure 20:
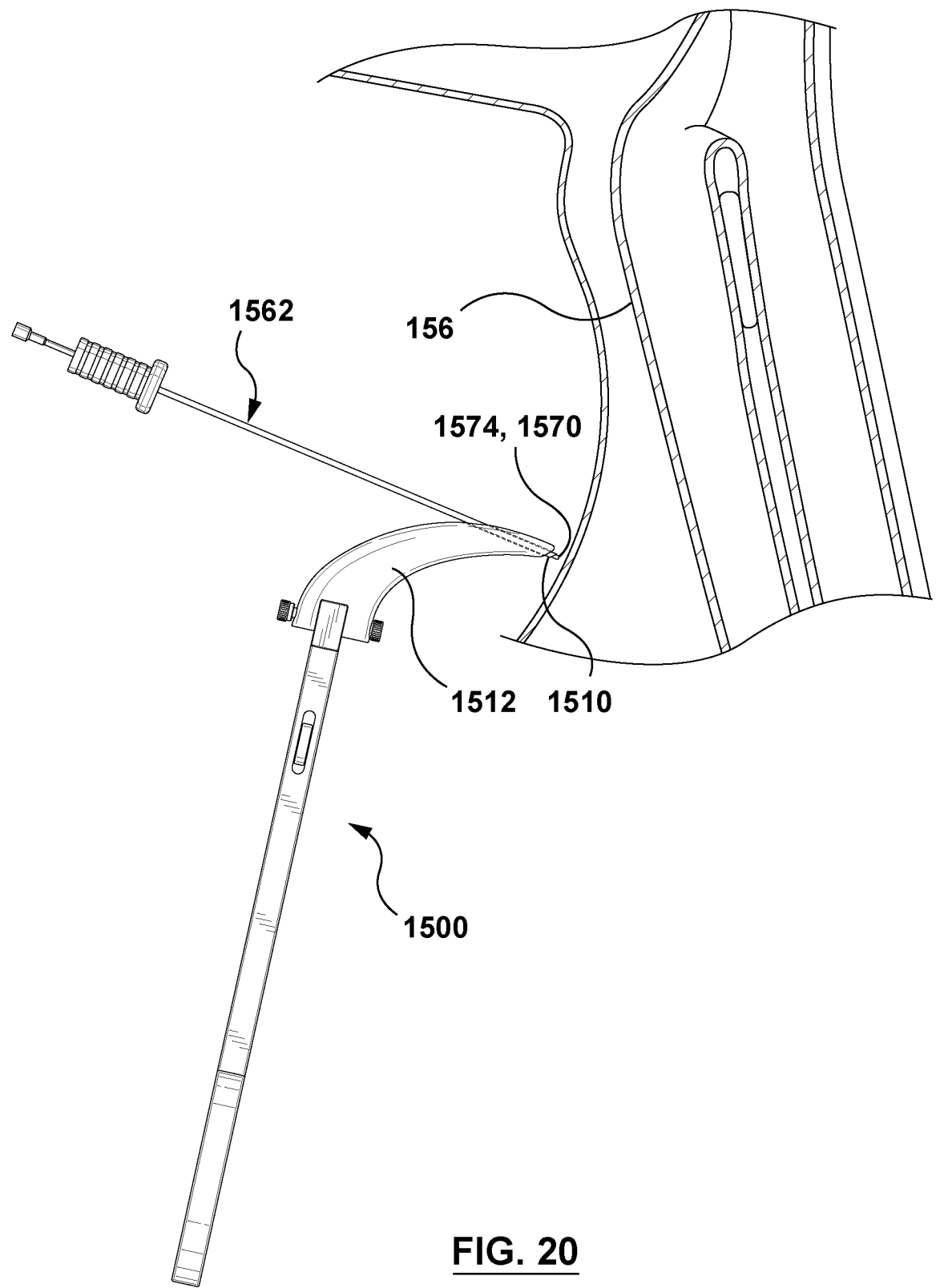
FIG. 20 is a schematic side view of the device of FIG. 15 in use, with a sharp tip of the device positioned to puncture the skin adjacent the trachea.
Figure 21:
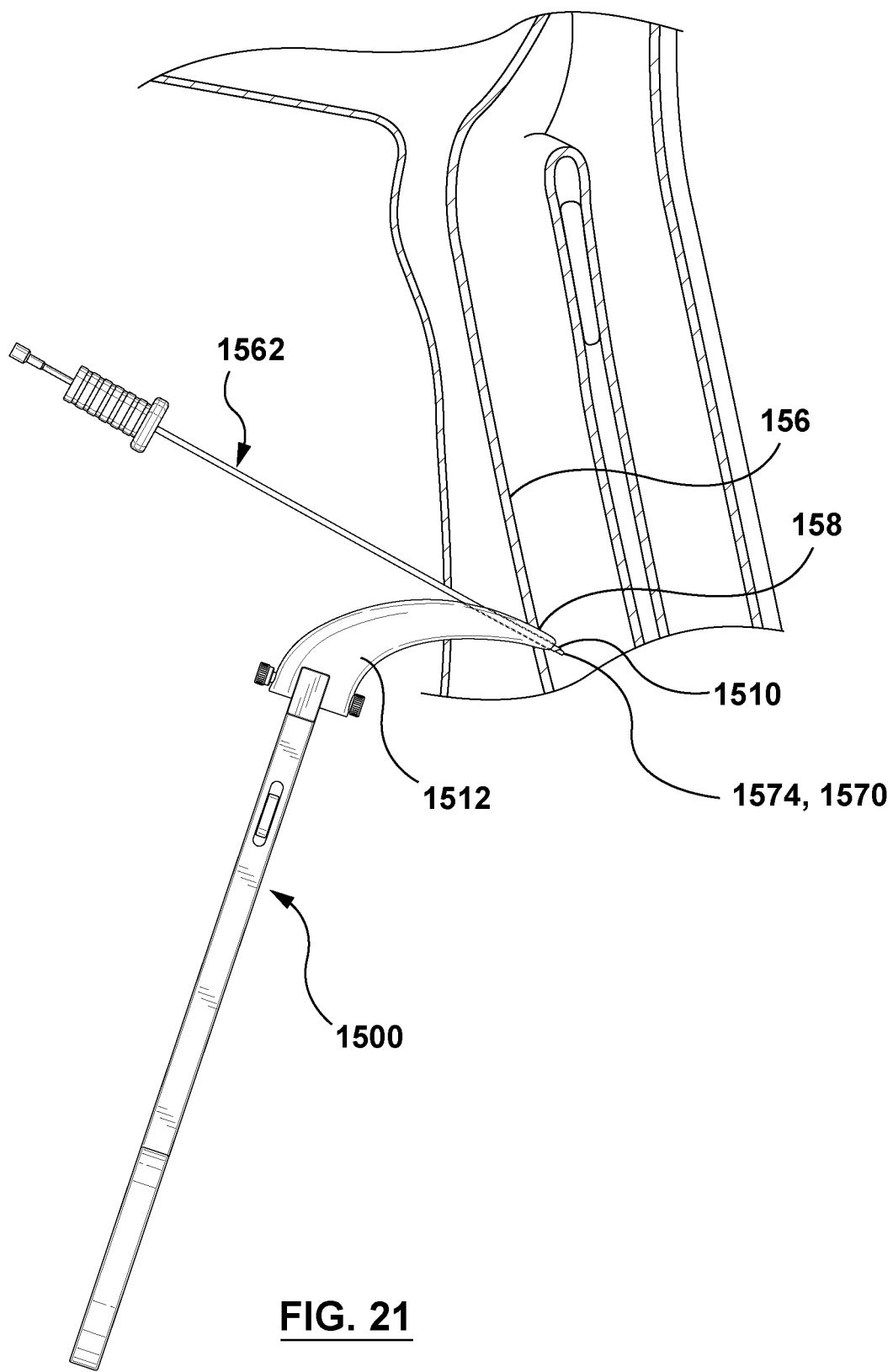
FIG. 21 is a schematic side view of the device of FIG. 15 in use, with the sharp tip of the device having just punctured the trachea.

Another method for creating a tracheostomy will now be described with reference to FIGS. 20 to 22. The method will be described with reference to device 1500; however, the device 1500 may be used according to other methods, and the method may be carried out with other devices.

The method may be carried out at the bedside, in the operating room, or in an emergency department. The method may begin after prepping of the patient, including sedation, preparation of the operative site, ultrasound, etc.

At the start of the method, the puncturing member 1562 may be positioned within the dilating member passage 1526, with the sharp tip 1510 extending from the dilating member distal end 1516, and with the stylet 1570 in the extended position. Referring to FIGS. 20 and 21, with the dilating member 1512 in the closed configuration and with the puncturing member 1562 within the dilating member 1512 so that the sharp tip 1510 protrudes therefrom, the device 1500 may be advanced towards the skin, so that the stylet distal end 1574 contacts the skin and moves towards the retracted position, exposing the sharp tip 1510. Continuing to advance the device, the sharp tip 110 may puncture the skin, subcutaneous tissue, and anterior wall 156 of the trachea, to create a puncture 158 in the trachea. After the sharp tip 1510 passes through the anterior wall 156, the force of the tissue on the stylet distal end 1574 will stop, and the stylet 1570 will spring back to the extended position. This springing may provide the surgeon or user with an indication (e.g. a tactile, visual, or auditory indication) that the trachea anterior wall 156 has been punctured. Advancement of the device 1500 may then be stopped.

A guidewire 132 (shown in FIG. 22) may then be advanced through the stylet passage and into the trachea, towards the patient's lungs.

Figure 22:
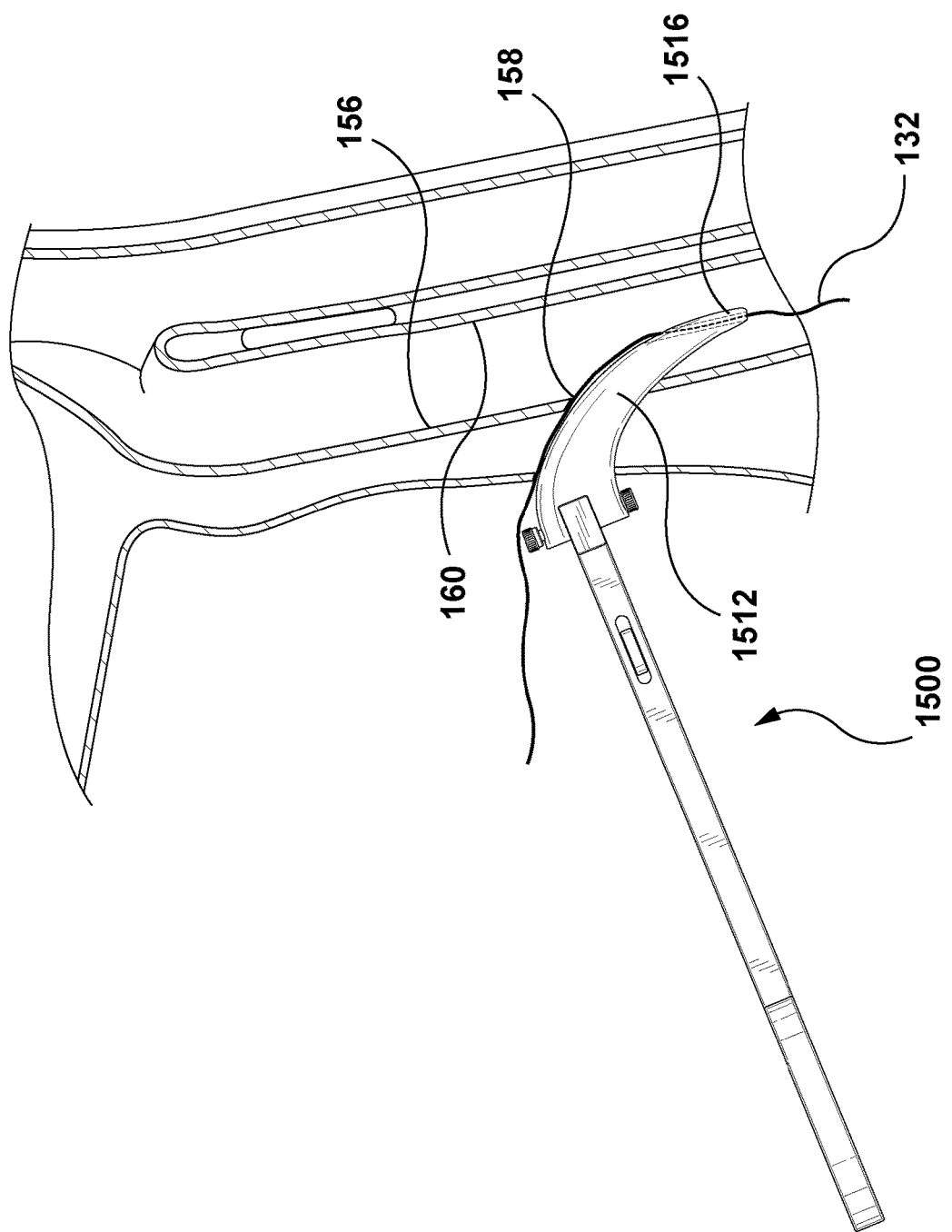
FIG. 22 is a schematic side view of the device of FIG. 15 in use, with the puncturing member removed from the dilating member, a guidewire received in the dilating member, and the dilating member being advanced into the trachea along a curved path.

Referring to FIG. 22, the puncturing member 1562 (not shown in FIG. 22) may then be withdrawn and removed from the dilating member 1512, and the dilating member 1512 may be advanced into the puncture 158, to dilate the puncture 158. The dilating member 1512 may be advanced along a curved path, so that the dilating member distal end 1516 is steered generally downwardly away from the posterior wall 160 of the trachea.

As described above with respect to FIGS. 13 and 14, the dilating member 1512 may then be actuated to spread the puncture 158 to an open state, and then may optionally be locked in the open configuration. With the dilating member 1512 in the open configuration, and the puncture 158 in the trachea in an open state, an introducer (not shown) may be advanced into the trachea, between the first dilating member side piece and second dilating member side piece. Due to the open state of the trachea, advancement of the introducer may be relatively safe and simple, because the surgeon can visualize the path of the introducer and ensure that the introducer is in the trachea and directed towards the lungs.

The device 1500 may then be removed from the patient, and a tracheotomy tube (not shown) may be advanced over the introducer.

Figure 23:
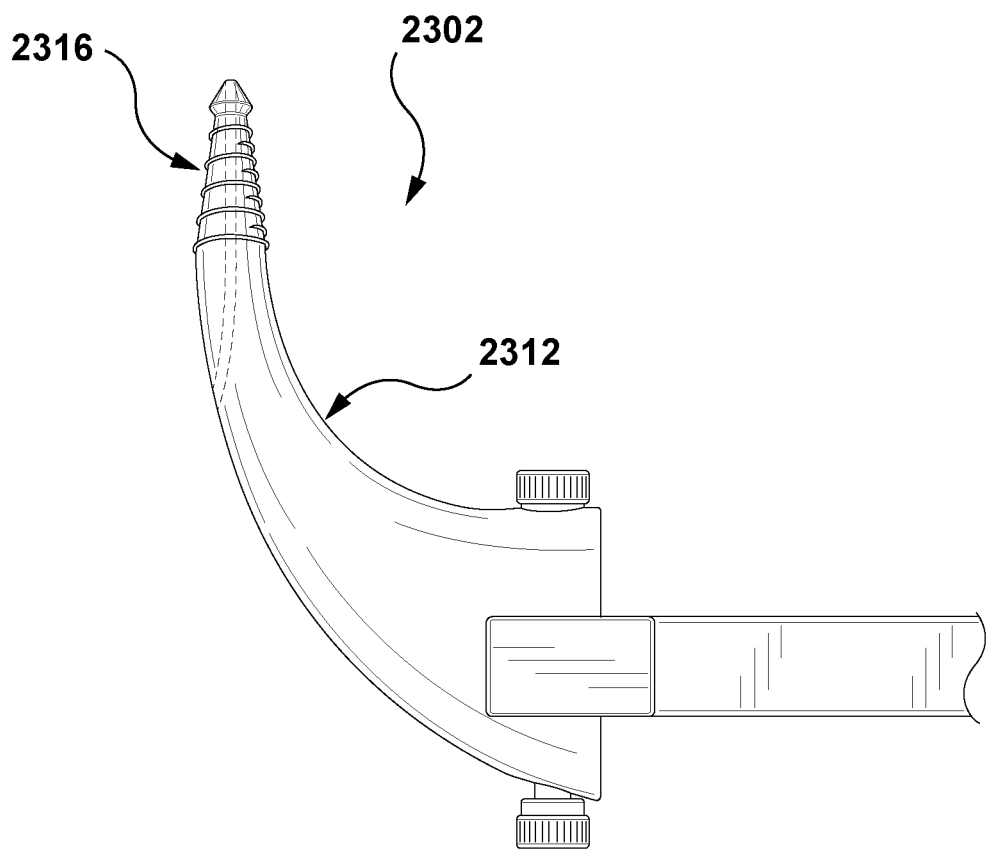
FIG. 23 is a perspective view of a head of another example tracheotomy device.

Referring now to FIG. 23, a head 2302 of another example tracheotomy device is shown. In FIG. 23, like features to the example of FIGS. 1 to 9 will be referred to with like reference numerals, incremented by 2200.

The head 2302 is similar to the head 102; however, the dilating member distal end 2316 is ribbed, in order to prevent unwanted slippage of the dilating member distal end 2316 when passing through the trachea. Furthermore, the dilating member 2312 is curved at a steeper angle than the dilating member 112.

While the above description provides examples of one or more processes or apparatuses, it will be appreciated that other processes or apparatuses may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be revisited.

I claim:

1. A tracheotomy device comprising:
   a) a head with a head proximal end and a head distal end, the head having (i) a dilating member having a first dilating member side piece with a first inner planar surface and a first outer rounded surface, and a second dilating member side piece with a second inner planar surface that faces the first inner planar surface and a second outer rounded surface, wherein the dilating member is moveable between a closed configuration in which the first dilating member side piece and the second dilating member side piece are adjacent and the first inner planar surface and second inner planar surface are in abutment, and an open configuration in which the first dilating member side piece is spaced from the second dilating member side piece, and wherein the dilating member has a dilating member proximal end and a dilating member distal end and tapers in cross-sectional area going in a direction from the dilating member proximal end towards the dilating member distal end and is curved between the dilating member proximal end and the dilating member distal end, (ii) a sharp tip at the head distal end for puncturing tissue, and (iii) a passage formed by the first dilating member side piece and the second dilating member side piece when the dilating member is in the closed configuration, wherein the passage extends from a proximal opening in the dilating member towards the dilating member distal end; and
   b) a gripping member connected to the head proximal end, wherein the gripping member comprises a first arm connected to the first dilating member side piece and a second arm connected to the second dilating member side piece, wherein the first arm is pivotably joined to the second arm, and the gripping member is actuatable by pivoting the first arm with respect to the second arm to move the dilating member between the closed configuration and the open configuration.

2. The tracheotomy device of claim 1, wherein the sharp tip is removable from the dilating member.

3. The tracheotomy device of claim 2, wherein the sharp tip is retractable from the head distal end towards the head proximal end.

4. The tracheotomy device of claim 1, wherein:
   the device further comprises an elongate puncturing member removably received in the passage and having a puncturing member distal end and a puncturing member proximal end, wherein the sharp tip is provided by the puncturing member distal end.

5. The tracheotomy device of claim 4, wherein:
   a) the puncturing member comprises (i) an elongate outer cannula having a cannula proximal end and a cannula distal end, wherein the cannula distal end provides the sharp tip, and (ii) an elongate inner stylet within the cannula; and
   b) the stylet has a blunt stylet distal end and an opposed stylet proximal end, and the stylet is moveable between an extended position wherein the stylet distal end is proud of the sharp tip, and a retracted position wherein the stylet distal end is shy of the sharp tip.

6. The tracheotomy device of claim 5, wherein the stylet is biased towards the extended position and is moveable from the extended position to the retracted position upon application of force on the stylet distal end in a proximal direction.

7. The tracheotomy device of claim 5, wherein the stylet has a stylet passage extending longitudinally therethrough and having an opening at the stylet distal end.

8. The tracheotomy device of claim 1, wherein the sharp tip comprises a first tip side piece connected to the first dilating member side piece, and a second tip side piece connected to the second dilating member side piece, and wherein when the dilating member is in the closed configuration, the first tip side piece is adjacent the second tip side piece, and when the dilating member is in the open configuration, the first tip side piece is spaced from the second tip side piece.

9. The tracheotomy device of claim 1, wherein the dilating member is lockable in the open configuration.

10. The tracheotomy device of claim 1, wherein the first dilating member side piece and second dilating member side piece each extend from the dilating member proximal end to the dilating member distal end.

11. The tracheotomy device of claim 1, wherein
the first arm has a first arm proximal end portion, a first arm central portion, and a first arm distal end portion, and the first arm distal end portion is connected to the first dilating member side piece, and ii) the second arm has a second arm proximal end portion, a second arm central portion and a second arm distal end portion, and the second arm distal end portion is connected to the second dilating member side piece; and
b) the first arm central portion is pivotably joined to the second arm central portion.

12. The tracheotomy device of claim 1, wherein the dilating member distal end is ribbed.

* * * * *